United States Patent
Norcross, Jr.

(10) Patent No.: US 9,464,976 B2
(45) Date of Patent: Oct. 11, 2016

(54) IN-LINE VISCOMETER WITH NO MOVING PARTS AND METHODS AND COMPUTER-READABLE MEDIA FOR MAINTAINING A DESIRED VISCOSITY

(75) Inventor: Robert A. Norcross, Jr., Newton, MA (US)

(73) Assignee: Saint Clair Systems, Inc., Washington, MI (US)

(*) Notice: Subject to any disclaimer, the term of this patent is extended or adjusted under 35 U.S.C. 154(b) by 660 days.

(21) Appl. No.: 13/223,855

(22) Filed: Sep. 1, 2011

(65) Prior Publication Data
US 2012/0084024 A1    Apr. 5, 2012

Related U.S. Application Data

(63) Continuation of application No. PCT/US2010/028446, filed on Mar. 24, 2010.

(60) Provisional application No. 61/162,786, filed on Mar. 24, 2009.

(51) Int. Cl.
| | | |
|---|---|---|
| *G01N 11/08* | (2006.01) | |
| *G01N 11/04* | (2006.01) | |
| *G01F 5/00* | (2006.01) | |

(52) U.S. Cl.
CPC ............ *G01N 11/08* (2013.01); *G01N 11/04* (2013.01); *G01F 5/00* (2013.01)

(58) Field of Classification Search
CPC .......... G01N 11/08; G01N 11/04; G01F 5/00
See application file for complete search history.

(56) References Cited

U.S. PATENT DOCUMENTS

| | | | |
|---|---|---|---|
| 3,903,840 A * | 9/1975 | Gemelli | 118/712 |
| 4,944,078 A * | 7/1990 | Nakade | 28/183 |
| 5,297,426 A * | 3/1994 | Kane et al. | 73/202 |
| 5,602,345 A | 2/1997 | Wenger et al. | |
| 5,661,232 A * | 8/1997 | Van Cleve et al. | 73/54.05 |
| 5,753,827 A * | 5/1998 | Cage | 73/861.356 |
| 6,073,483 A | 6/2000 | Nitecki et al. | |
| 6,378,364 B1 * | 4/2002 | Pelletier et al. | 73/152.47 |
| 6,901,788 B2 * | 6/2005 | Han et al. | 73/53.05 |
| 2007/0220995 A1 * | 9/2007 | Kishiro et al. | 73/861.28 |
| 2008/0016957 A1 * | 1/2008 | Suzuki | 73/204.21 |
| 2009/0193889 A1 * | 8/2009 | Waid et al. | 73/32 A |
| 2010/0089174 A1 * | 4/2010 | Van Cleve | 73/861.357 |

FOREIGN PATENT DOCUMENTS

| | | |
|---|---|---|
| CN | 100401022 | 7/2008 |
| WO | 97/33150 A2 | 9/1997 |

OTHER PUBLICATIONS

Volumetric flow rate Wikipedia, Nov. 17, 2007; available at https://web.archive.org/web/20071117135615/http://en.wikipedia.org/wiki/Volumetric_flow_rat.*
International Search Report for International Application No. PCT/US2010/028446 (May 12, 2010).
Written Opinion for International Application No. PCT/US2010/028446 (May 12, 2010).

* cited by examiner

*Primary Examiner* — Andrew Schechter
*Assistant Examiner* — John Kuan
(74) *Attorney, Agent, or Firm* — Parker Ibrahim & Berg LLC; Stephen D. LeBarron

(57) ABSTRACT

The present invention relates to in-line viscometers with no moving parts for monitoring the viscosity of fluids. One embodiment of the invention is a viscometer including a first tube, a second tube, a first flow metering device coupled with the first tube, a second flow metering device coupled with the second tube. The second tube is larger in diameter than the first tube. Another embodiment is directed to a method for maintaining a desired viscosity during a process.

15 Claims, 5 Drawing Sheets

IN-LINE VISCOMETER WITH NO MOVING PARTS AND METHODS AND COMPUTER-READABLE MEDIA FOR MAINTAINING A DESIRED VISCOSITY

RELATED APPLICATIONS

This application is a continuation under 35 U.S.C. §120 of International Application No. PCT/US2010/028446, filed Mar. 24, 2010, which claims priority to U.S. Provisional Patent Application Ser. No. 61/162,786, filed Mar. 24, 2009. The entire contents of each of these applications are hereby incorporated by reference herein.

TECHNICAL FIELD

The present invention relates to in-line viscometers with no moving parts for monitoring the viscosity of fluids in applications such as printing and manufacturing.

BACKGROUND

Viscosity control is essential in many of today's manufacturing and printing processes. Viscosity is the measure of the resistance of a fluid to deformation by either shear stress or extensional stress, but is commonly perceived as the "thickness" or resistance to flow of a fluid. Viscosity can be an important quality of a finished product (e.g., a lubricant, paint, or ink) or can affect a finished product (e.g., printed material). Perhaps more importantly, an inappropriate viscosity can adversely affect modern industrial equipment. For example, if the viscosity of printing ink falls outside of an acceptable viscosity ranges, not only is print quality affected, but the printing press can also become fouled.

Various viscometers have been proposed over past century in which measuring equipment directly contacts the fluid to be measured. Such equipment can be problematic for several reasons. First, the moving parts are difficult and time consuming to clean. This adds time effort to cleanings of manufacturing equipment either required periodically or when a manufacturing line is changed from one product to another. Second, the moving parts present additional risk of mechanical failure.

Accordingly, it would be desirable to provide a viscometer with no moving parts that is both durable and easy to clean.

SUMMARY OF THE INVENTION

The present invention relates to in-line viscometers with no moving parts for monitoring the viscosity of fluids.

One aspect of the invention provides a viscometer including: a first tube having a first cross-sectional area; a second tube having a second-cross sectional area; a first flow metering device coupled with the first tube; and a second flow metering device coupled with the second tube. The second cross-sectional area of the second tube is larger than first the cross-sectional area of the first tube.

This aspect can have a variety of embodiments. The second tube can include a restrictor having a third cross-sectional area. The third cross-sectional area of the restrictor can be substantially equal to the first cross-sectional area of the first tube. The third cross-sectional area of the restrictor can be greater than the first cross-sectional area of the first tube. The third cross-sectional area of the restrictor can be less than the first cross-sectional area of the first tube.

The viscometer can include an inlet coupled to the first tube and the second tube by a first connector having a first chamber; and an outlet coupled to the first tube and the second tube by a second connector having a second chamber. The first chamber and the second chamber can each comprise a smooth internal geometric feature.

The first flow metering device can be a first ultrasound flow meter and the second flow metering device can be a second ultrasound flow meter. The first ultrasound flow meter and the second ultrasound flow meter can be transit time flow meters. The first ultrasound flow meter and the second ultrasound flow meter can be Doppler flow meters.

The first tube and the second tube can be greater than or equal to about 6" in length. The first tube and the second tube can be greater than or equal to about 12" in length. The ratio of the second cross-sectional area of the second tube to the first cross-sectional area of the first tube can be about 16:9 or greater. The ratio of the second cross-sectional area of the second tube to the first cross-sectional area of the first tube can be about 4:1 or greater.

The viscometer can include an electronic device communicatively coupled with the first flow metering device and the second flow metering device. The electronic device can be configured to compute the ratio between the flow rate measured by the second flow metering device and the flow rate measured by the first flow metering device.

The electronic device can be configured to communicate an alert when the ratio between the flow rates exceeds a defined range. The electronic device can be configured to suspend a process when the ratio between the flow rates exceeds a defined range.

Another aspect of the invention provides a method for maintaining a desired viscosity during a process. The method includes: verifying that a fluid used in the process has a desired viscosity; passing a portion of the fluid through a viscometer including a first tube having a first cross-sectional area, a second tube having a second-cross sectional area, a first flow metering device coupled with the first tube, and a second flow metering device coupled with the second tube; measuring a first flow rate through the first flow tube and a second flow rate through the second tube; computing an initial ratio between the second flow rate and the first flow rate; remeasuring the first flow rate through the first flow tube and the second flow rate through the second tube; computing subsequent ratios between the second flow rate and the first flow rate; and detecting a deviation of one of the subsequent ratios from the initial ratio. The second cross-sectional area of the second tube is larger than first the cross-sectional area of the first tube.

This aspect can have a variety of embodiments. The method can include communicating an alert when the deviation is detected. The method can include adjusting the viscosity of the fluid when the deviation is detected. The method can be a computer-implemented method.

Another aspect of the invention provides a computer-readable medium whose contents cause a computer to perform a method for maintaining a desired viscosity during a process. The method includes: verifying that a fluid used in the process has a desired viscosity; passing a portion of the fluid through a viscometer including a first tube having a first cross-sectional area, a second tube having a second-cross sectional area, a first flow metering device coupled with the first tube, and a second flow metering device coupled with the second tube; measuring a first flow rate through the first flow tube and a second flow rate through the second tube; computing an initial ratio between the second flow rate and the first flow rate; remeasuring the first flow rate through the first flow tube and the second flow rate through the second tube; computing subsequent ratios between the second flow rate and the first flow rate; and detecting a deviation of one of the subsequent ratios from the initial ratio. The second cross-sectional area of the second tube is larger than first the cross-sectional area of the first tube.

This aspect can have a variety of embodiments. The computer-readable medium can be non-transitory and tangible.

FIGURES

For a fuller understanding of the nature and desired objects of the present invention, reference is made to the following detailed description taken in conjunction with the accompanying drawing figures wherein like reference characters denote corresponding parts throughout the several views and wherein.

DESCRIPTION OF THE INVENTION

The present invention relates to in-line viscometers with no moving parts for monitoring the viscosity of fluids. The viscometer is ideal for a variety of applications including industrial processes, printing, manufacturing, food processing, medical devices, and the like.

Figure 1:
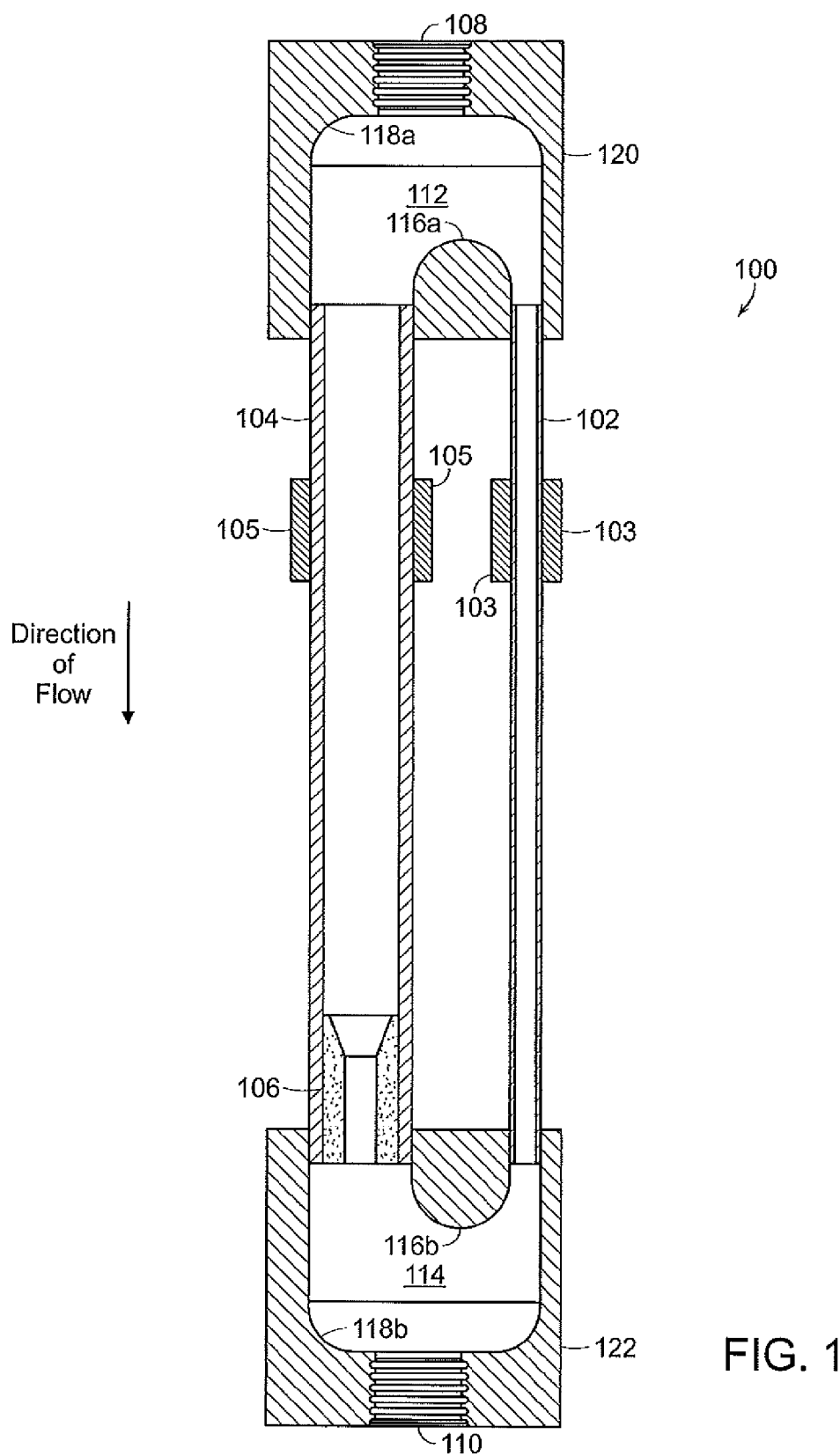
FIG. 1 is a cross-sectional view of one embodiment of a viscometer with no moving parts.

As depicted in FIG. 1, one embodiment of the invention is an in-line viscometer 100 including a first tube 102, a second tube 104, a first flow metering device 103 coupled with the first tube 102, a second flow metering device 105 coupled with the second tube 104. The second tube 104 is larger in diameter than the first tube 102. In some embodiments, the second tube 104 includes a diameter-reducing restrictor 106, which causes a small pressure drop, thereby further affecting the ratio of velocities between fluids in tubes 102 and 104.

Tubes 102 and 104 can be generally cylindrical, and have other cross-sectional shape such as a square, a rectangle, a triangle, a circle, an oval, a polygon, a parallelogram, a rhombus, an annulus, a crescent, a semicircle, an ellipse, a super ellipse, a deltoid, and the like.

Tubes 102 and 104 are connected to inlet 108 and outlet 110 by chambers 112 and 114 formed in connectors 120 and 122, respectively. Inlet 108 and outlet 110 can be designed for coupling the viscometer with a fluid source and sink, for example, by threading, soldering, brazing, welding, compression, flaring, crimping, press fitting, solvent welding, heat fusion, elastomeric sealing, and the like.

Chambers 112, 114 can preferably include one or more smooth geometric features 116*a*, 116*b*, 118*a*, 118*b* such as curves, fillets, chamfers, and bullnoses to promote fluid flow with minimal turbulence and/or cavitation.

Tubes 102 and 104 and connectors 120 and 122 can comprise any material known to those of skill in the art for the transport of fluid including copper, steel (including unfinished or galvanized), cast iron, brass, other metals and metal alloys, polyvinyl chloride (PVC), chlorinated polyvinyl chloride (CPVC), cross-linked high-density polyethylene (PEX), polybutylene (PB), acrylonitrile butadiene styrene (ABS), and the like. Such material should be substantially inert to the fluid being transmitted through viscometer 100.

In some embodiments, tubes 102 and 104 are relatively thin walled to allow for greater acoustical transparency, particularly when the first and second flow metering devices 103 and 104 are ultrasound flow metering devices as discussed in various embodiments herein. However, in other embodiments, such as embodiments adapted to high pressure applications, tubes 102 and 104 are constructed of materials and thickness capable of withstanding the particular operational pressures.

In other embodiments, the interior and/or exterior of the tube are coated with materials that promote longevity of the tube. Such coatings include corrosion resistant substances include 316 L steel, enamels, and alloys available under the HASTELLOY® trademark from Haynes International, Inc. of Kokomo, Ind. Other coatings include polytetrafluoroethylene (PTFE), available, for example, under the TEFLON® trademark from E.I. Du Pont de Nemours and Company of Wilmington, Del. Such coatings are well known in the art and the invention is not restricted to coatings presently known, but also extends to future discovered coatings and methods.

Tubes 102 and 104 are of a sufficient length to accommodate the flow metering devices 103 and 105 and, when used, a diameter-reducing restrictor 106. While no particular length is required, longer length tubes (e.g., 6 and 12 inch lengths) promote increased sensitivity to variations in viscosity as compared to shorter length tubes (e.g., 2 inch lengths).

As discussed, tube 104 has a larger internal diameter (ID) than tube 102. Although specific IDs or ratio of IDs are generally not required for operation of the viscometer 100, experimentation suggests that viscometers with larger ratios between the ID of tube 104 over the ID of tube 102 are more sensitive to changes in viscosity. For example, a viscometer having IDs of ¾" and ¼" was found to be more sensitive than a viscometer having IDs of ½" and ⅜". (The cross-sectional area is approximately 0.441 square inches for a cylindrical tube having a diameter of ¾" and approximately 0.110 square inches for a cylindrical tube having a diameter of ¼", resulting a cross-sectional surface area ratio of about 4:1. The cross-sectional area ratio for cylindrical tubes having diameters of ½" and ⅜" is about 16:9.)

In some embodiments, diameter-reducing restrictor 106 is an insert that is placed in tube 104. For example, restrictor 106 can be composed any material capable of withstanding the flow of the liquid that will flow through the viscometer 100. Exemplary materials include the materials discussed above in the context of tubes 102 and 104. In some embodiments, restrictor 106 is comprised of a nonporous material for sanitary benefits, but this not required. Restrictor 106 is generally sized to match the ID of tube 104, however the interface between restrictor 106 and tube 104 need not be fluid-tight. A fluid-tight seal can be formed by using an adhesive or sealant such as epoxy to bond restrictor 106 to tube 104. Other methods for bonding restrictor 106 to tube 104 include welding, brazing, press fitting, crimping and the like.

Figure 2:
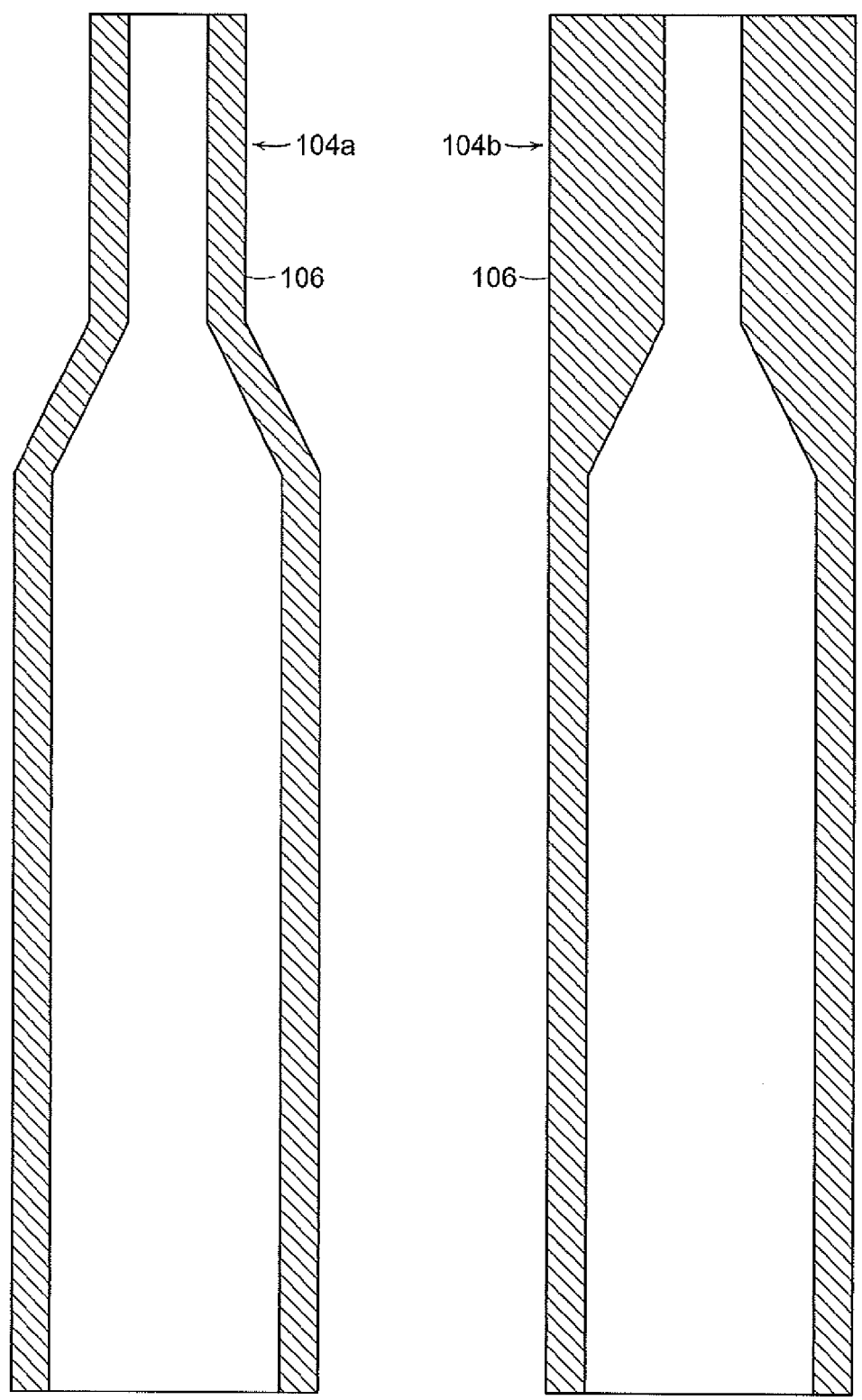
FIG. 2 is a cross-sectional view of various configurations of a second tube with a diameter-reducing restrictor.

In other embodiments, diameter-reducing restrictor 106 is integrally formed with tube 104. For example, as depicted in FIG. 2, tube 104*a* can be formed such that it has a generally constant thickness as well as a restricting portion 106. In another example, tube 104 is machined such as tube 104b contains a larger ID portion (with a thin wall) and a smaller ID portion 106 (with a thick wall). In other embodiments, the restrictor can be attached to the end of tube 104.

The viscometer includes at least one flow meter 103, 105 coupled to each tube 102, 104 for measuring the fluid velocity through tubes 102 and 104. Flow meters 103, 105 may be located, in whole, in part, or in combination, on the interior or exterior of tubes 102 and 104. Flow meters 103, 105 are preferably located upstream from restrictor 106, in embodiments of the viscometer 100 comprising a restrictor 106.

In certain embodiments, the flow meters 103, 105 are ultrasound flow meters such as transit time flow meters and Doppler flow meters. Transit time flow meters measure the time of flight difference between an ultrasonic pulse sent in the flow direction and an ultrasonic pulse sent opposite the flow direction. Doppler flow meters determine velocity by measuring the Doppler shift off of particles, bubbles, or turbulence in the fluid. Ultrasound flow meters are available from a variety of sources including, but not limited to Precision Flow Ltd. of Buckinghamshire, United Kingdom; Sierra Instruments of Monterey, Calif.; RS Hydro of Worcestershire, United Kingdom; EESiFlo North America of Mechanicsburg, Pa.; Signal Processing SA of Savigny, Switzerland; Met-Flow S.A. of Lausanne, Switzerland; and Katronic Technologies Ltd. of Warwickshire, United Kingdom.

Flow meters 103, 105 can be configured in a variety of ways. For example, an ultrasound flow meter comprising a transducer and a receiver can be configured such that the transducer and flow meter are located approximately 180° apart. Alternatively, the transducer and receiver can be configured so that the path between the transducer and receiver forms a chord across a circular cross-section of the tubes 102 and 104. Multiple pairs of transducers and receivers can be configured, for example, as described in U.S. Pat. No. 4,078,428 to Baker et al. and U.S. Pat. No. 4,102,186 to Brown, the contents of which are hereby incorporated herein by reference.

Figure 4:
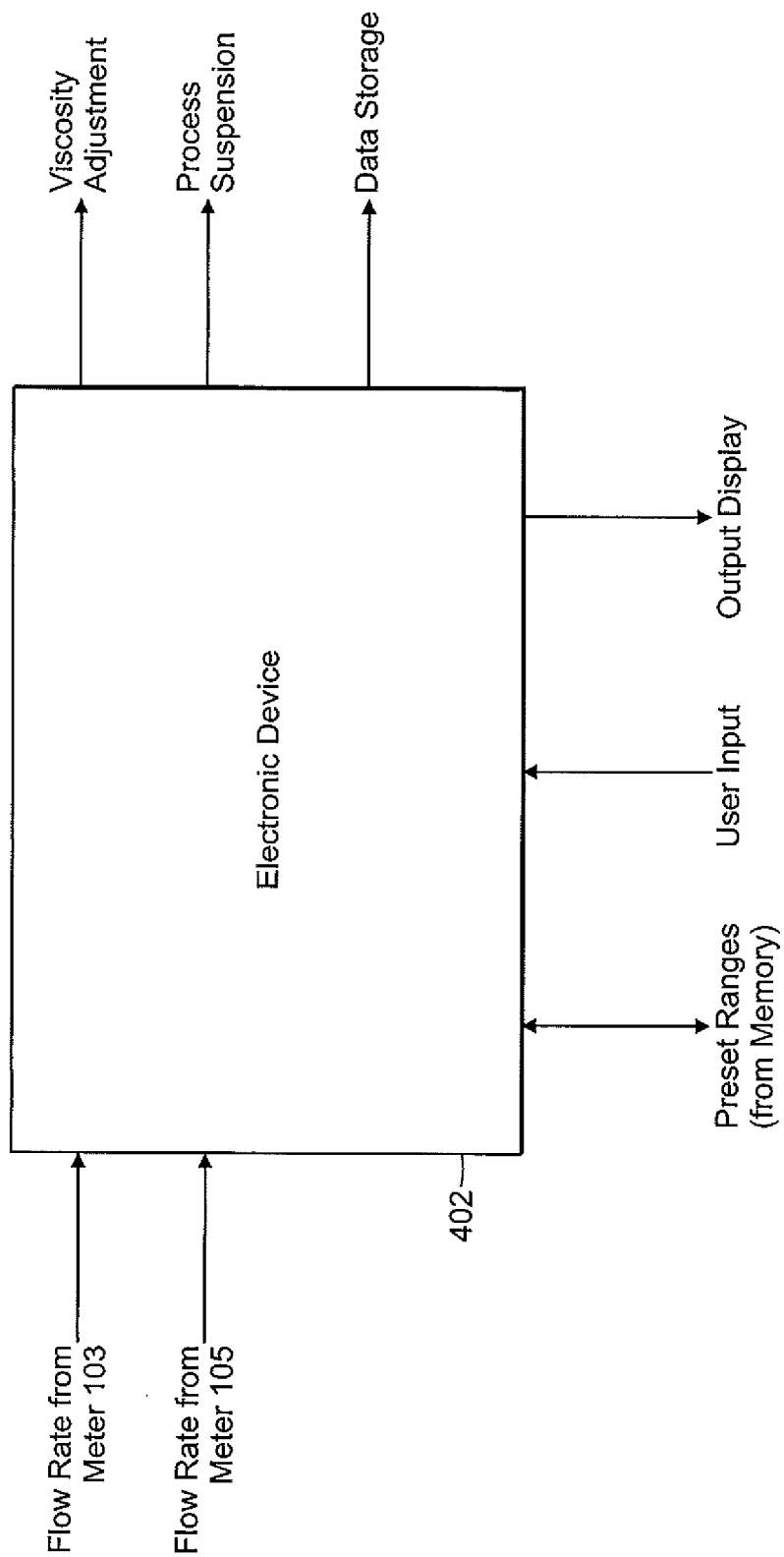
FIG. 4 is an input/output diagram for an electronic device adapted to process and monitor the measurements produced by viscometer described herein.

In some embodiments, flow sensors 103, 105 are communicatively coupled with an electronic device to facilitate calculation of the flow rate ratio. Suitable devices include dedicated hardware such as an arithmetic logic unit or a computer, as is appreciated by those of skill in the art. A schematic of one suitable device is provided in FIG. 4. Flow sensors 103, 105 can communicate with electronic device 402 by wired or wireless means including, but not limited to, serial cable, Ethernet, LAN, WAN, Internet, Intranet, Virtual Private Network, Wi-Fi, Bluetooth, infrared, and the like now known and later developed. The electronic device 402 may include further communication devices such as visual and audio alarms and graphic user interfaces (GUIs) to alert a user when viscosity exceeds an acceptable range. The acceptable range may vary depending on the application and may be set by the user and/or another system. In another embodiment, the electronic device is configured to suspend a process (e.g., a printing process) when the viscosity exceeds an acceptable range so as to prevent damage to the other equipment or waste of materials.

The electronic device 402 may include communications or storage devices to communicate and/or record the date collected and produced. Suitable electronic devices for the management of viscosity are available, for example, from Norcross Corporation of Newton, Mass.

In other embodiments, flow meters 103, 105 display the flow values either through an analog or digital display device, allowing for the manual calculation and monitoring of the ratio.

Figure 3:
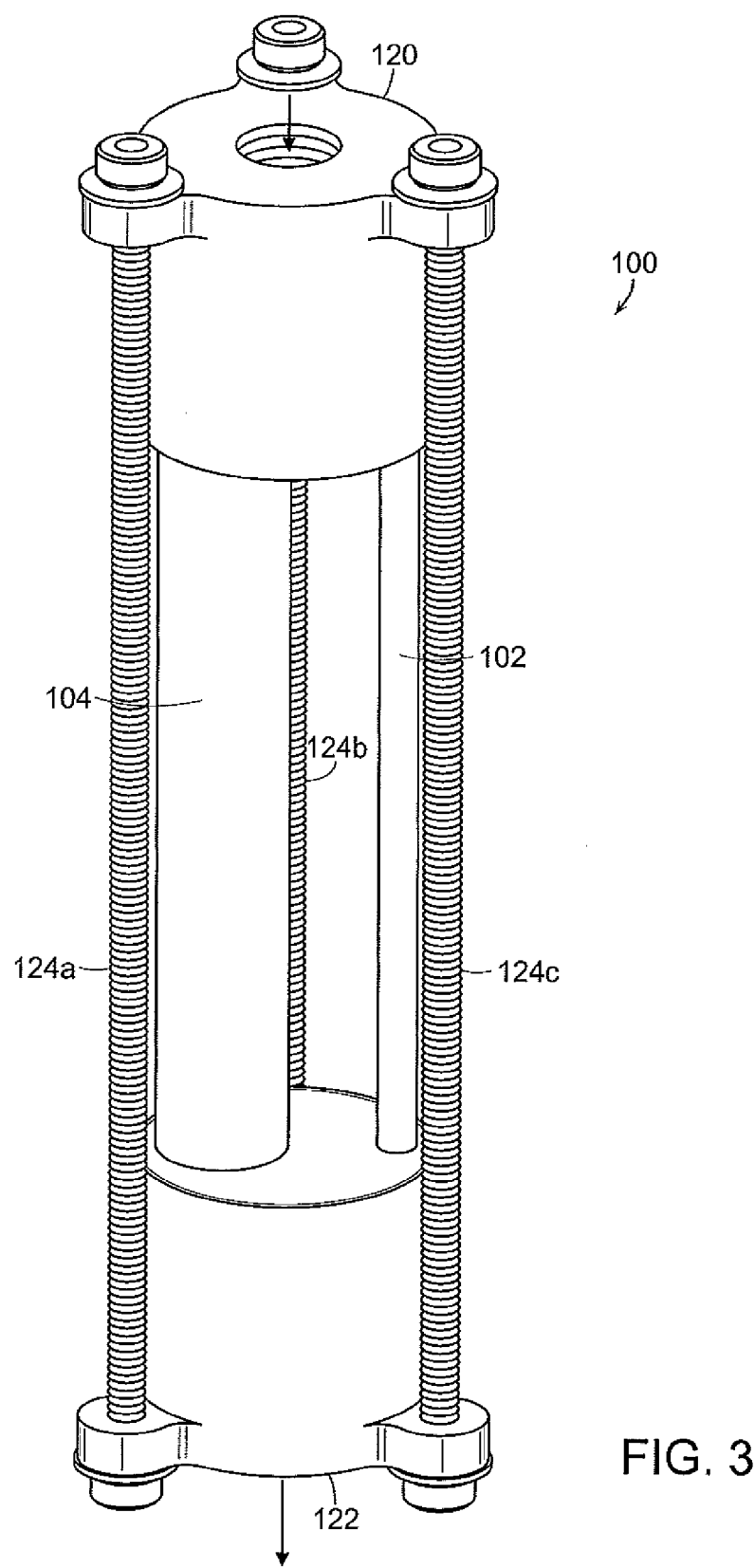
FIG. 3 is a perspective view of a viscometer with no moving parts in accord with one embodiment of the invention.

FIG. 3 is a perspective view of an exemplary embodiment of viscometer 100. In some embodiments, a seal is formed between tubes 102 and 104 and connectors 120 and 122 by force applied to connectors 120 and 122 by tension member(s) 124a, 124b, 124c. Tension members 124 can be bolts, screws, threaded rod, rivets, or other device as appreciated by those of skill in the art.

Figure 5:
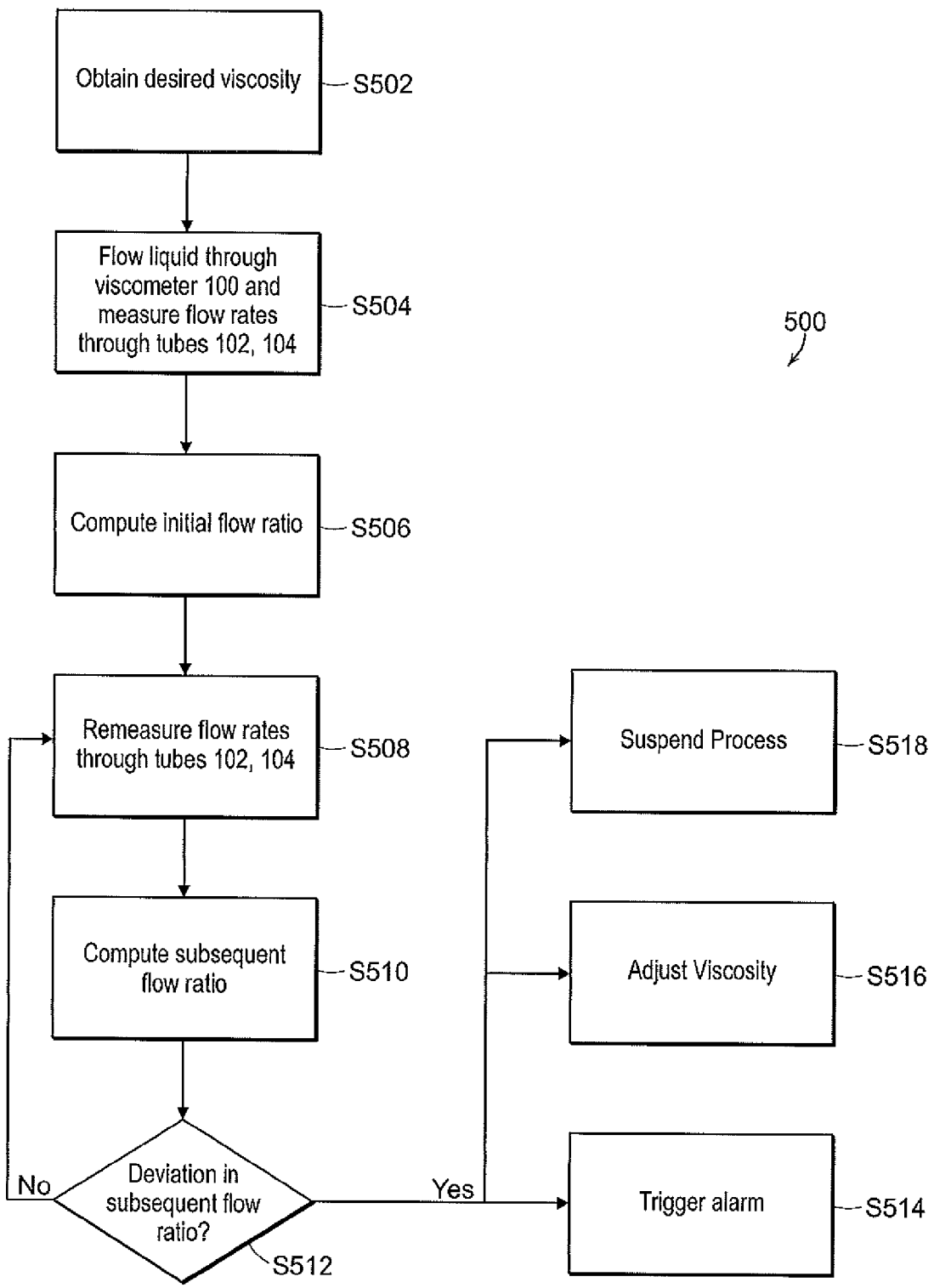
FIG. 5 is flow chart depicting a method for monitoring the viscosity of a liquid using a viscometer described herein.

Viscosity is a relative value. Accordingly, the inventions described herein can be used to measure deviations from a desired viscosity using the method 500 depicted in FIG. 5. In this embodiment, a desired viscosity is first obtained using conventional viscometers (S502). For example, viscosity may be measured with a SHELL CUP® viscometer, a stainless steel cup which drains through a capillary at the bottom of the cup. The entire cup is submerged in a sample, then raised and held above the surface of the sample. The time in seconds from the moment the top of the cup emerges from the sample until the first break in the stream from the capillary orifice is the measure of viscosity. SHELL CUP® viscometers are available from Norcross Corporation of Newton, Mass. If measurements using a SHELL CUP® viscometer indicate that the sample does not have the desired viscosity, the viscosity can be modified by steps known to those of skill in the art such as added solvent or solute, adjusting the temperature of the sample, and the like.

Once the desired viscosity is achieved, the sample is flowed through the viscometer and the flow ratio between tubes 102 and 104 is measured (S504, S506). The viscometer is calibrated to the measured ratio, which corresponds to the desired viscosity. The viscometer monitors fluctuations in the ratio, wherein increases in the ratio indicate a drop in viscosity and decreases in the ratio indicate an increase in viscosity (S508, S510, S512). If a deviation is detected (S512), a number of steps can be taken including triggering an alarm (S514), adjusting the sample to restore the desired viscosity (S516), and suspending the process (S518).

The inventions herein are further explained through the following working examples, which are intended to further illustrate certain embodiments, but not to limit the invention in any way.

Working Example 1

A comparison of the effect of tube 102, 104 length on viscometer sensitivity was conducted. Three viscometers have tubes lengths of 2", 6", and 12" were assembled. Each viscometer included a first tube with a ¼" ID and a second (unrestricted) tube with a ¾" ID. Three fluids, having known viscosities of 10 cP, 40 cP, and 70 cP were passed through each viscometer under identical pumping and environmental conditions. Flow rates (in liters/minute) were measured and are summarized in Table 1 below.

TABLE 1

|  | Viscometer A | | Viscometer B | | Viscometer C | |
| --- | --- | --- | --- | --- | --- | --- |
| Viscosity | 2" length ¼" ID | 2" length ¾" ID | 6" length ¼" ID | 6" length ¾" ID | 12" length ¼" ID | 12" length ¾" ID |
| 10 cP | 2.1079 | 27.5342 | 1.5446 | 24.6913 | 1.0765 | 22.2950 |
| 40 cP | 1.3436 | 23.2318 | 0.6318 | 18.6661 | 0.3353 | 14.9391 |
| 70 cP | 0.9568 | 20.9864 | 0.3786 | 15.6683 | 0.1938 | 11.4533 |

The ratios between the flow rate in the first tube (having the ¼" ID) and the second tube (having the ¾" ID) are summarized below along with the percentage difference between the ratios calculated for fluids having a viscosity of 10 cP and 70 cP.

TABLE 2

| Viscosity | Viscometer A:<br>2" length<br>¼" ID vs. ¾" ID | Viscometer B:<br>6" length<br>¼" ID vs. ¾" ID | Viscometer C:<br>12" length<br>¼" ID vs. ¾" ID |
|---|---|---|---|
| 10 cP | 0.07656 | 0.06256 | 0.04828 |
| 40 cP | 0.05784 | 0.03385 | 0.02244 |
| 70 cP | 0.04559 | 0.02417 | 0.01692 |
| Percentage Change between 10 cP and 70 cP | 68% | 159% | 185% |

As shown in Table 2, viscometers having 6" and 12" tubes demonstrated a marked increase in sensitivity (magnitude of change in ratio as a result of change in viscosity) over viscometers with 2" tubes.

Working Example 2

A viscometer with a second tube having a 1" ID and a ¼" ID restrictor located 2" downstream in a 16" tube was constructed to measure the effect of a restrictor on viscometer sensitivity. The flow rates (L/min) and ratios for each pipe are provided in Table 3.

TABLE 3

| | Flow Rate | | |
|---|---|---|---|
| Viscosity | ¼" ID Unrestricted Tube | 1" ID Tube with ¼" ID Restrictor | Flowrate Ratio (Restricted over Unrestricted) |
| 10 cP | 1.1000 | 2.7603 | 0.3986 |
| 40 cP | 0.3301 | 2.4525 | 0.1346 |
| 70 cP | 0.1890 | 2.1560 | 0.0877 |

The viscometer exhibited a 355% difference between fluids having viscosities of 10 cP and 70 cP, demonstrating that the use of a restrictor improves the sensitivity of the viscometer.

The foregoing specification and the drawings forming part hereof are illustrative in nature and demonstrate certain preferred embodiments of the invention. It should be recognized and understood, however, that the description is not to be construed as limiting of the invention because many changes, modifications and variations may be made therein by those of skill in the art without departing from the essential scope, spirit or intention of the invention.

The invention claimed is:

1. A viscometer comprising:
a first tube having a first cross-sectional area;
a second tube having a second-cross sectional area, wherein the second cross-sectional area of the second tube is larger than the first cross-sectional area of the first tube;
a restrictor disposed in the second tube;
a first chamber formed between an inlet of the viscometer and an inlet of the first and second tubes respectively, the first chamber having a wider diameter than the inlet of the viscometer;
a second chamber formed between an outlet of the viscometer and an outlet of the first and second tube respectively, the second chamber having a wider diameter than the outlet of the viscometer;
a first ultrasound flow metering device coupled with the first tube, the first ultrasound flow metering device measuring a first velocity of fluid flowing through the first tube; and
a second ultrasound flow metering device coupled with the second tube, the second ultrasound flow metering device measuring a second velocity of fluid flowing through the second tube.

2. The viscometer of claim 1, wherein the restrictor has a third cross-sectional area.

3. The viscometer of claim 2, wherein the third cross-sectional area of the restrictor is substantially equal to the first cross-sectional area of the first tube.

4. The viscometer of claim 2, wherein the third cross-sectional area of the restrictor is greater than the first cross-sectional area of the first tube.

5. The viscometer of claim 2, wherein the third cross-sectional area of the restrictor is less than the first cross-sectional area of the first tube.

6. The viscometer of claim 1, wherein the first chamber and the second chamber each comprises a smooth internal geometric feature.

7. The viscometer of claim 1, wherein the first ultrasound flow meter and the second ultrasound flow meter are transit time flow meters.

8. The viscometer of claim 1, wherein the first ultrasound flow meter and the second ultrasound flow meter are Doppler flow meters.

9. The viscometer of claim 1, wherein the first tube and the second tube are greater than or equal to about 6" in length.

10. The viscometer of claim 1, wherein the first tube and the second tube are greater than or equal to about 12" in length.

11. The viscometer of claim 1, wherein the ratio of the second cross-sectional area of the second tube to the first cross-sectional area of the first tube is about 16:9 or greater.

12. The viscometer of claim 1, wherein the ratio of the second cross-sectional area of the second tube to the first cross-sectional area of the first tube is about 4:1 or greater.

13. The viscometer of claim 1 further comprising: an electronic device communicatively coupled with the first ultrasound flow metering device and the second ultrasound flow metering device, the electronic device configured to compute a ratio between a second flow rate associated with the second velocity measured by the second ultrasound flow metering device and a first flow rate associated with a first velocity measured by the first ultrasound flow metering device.

14. The viscometer of claim 13 wherein the electronic device is configured to communicate an alert when the ratio between the first flow rate and second flow rate exceeds a defined range.

15. The viscometer of claim 13 wherein the electronic device is configured to suspend a process when the ratio between the first flow rate and second flow rate exceeds a defined range.

* * * * *